(12) United States Patent
Yukimura et al.

(10) Patent No.: US 8,716,375 B2
(45) Date of Patent: May 6, 2014

(54) ORGANOSILICON COMPOUND AS WELL AS RUBBER COMPOSITION, TIRE PRIMER COMPOSITION, PAINT COMPOSITION AND ADHESIVE USING THE SAME

(75) Inventors: Noriaki Yukimura, Kodaira (JP); Seiichi Kato, Tokyo (JP); Satoshi Horie, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 80 days.

(21) Appl. No.: 13/321,469

(22) PCT Filed: Apr. 22, 2010

(86) PCT No.: PCT/JP2010/002933
§ 371 (c)(1),
(2), (4) Date: Dec. 9, 2011

(87) PCT Pub. No.: WO2010/134266
PCT Pub. Date: Nov. 25, 2010

(65) Prior Publication Data
US 2012/0108718 A1   May 3, 2012

(30) Foreign Application Priority Data
May 20, 2009   (JP) .................................. 2009-122322

(51) Int. Cl.
C08K 5/549 (2006.01)
C08L 7/00 (2006.01)
C08L 9/00 (2006.01)
C07F 7/18 (2006.01)

(52) U.S. Cl.
USPC ............. 524/95; 524/108; 524/188; 556/407; 556/408

(58) Field of Classification Search
USPC ............. 524/95, 108, 188; 556/413, 407, 408
See application file for complete search history.

(56) References Cited

U.S. PATENT DOCUMENTS

| | | | |
|---|---|---|---|
| 3,842,111 A | 10/1974 | Myer-Simon et al. | |
| 3,873,489 A | 3/1975 | Thurn et al. | |
| 3,997,581 A * | 12/1976 | Pletka et al. | 556/408 |
| 8,183,403 B2 * | 5/2012 | Yukimura et al. | 556/406 |
| 2007/0066760 A1 | 3/2007 | Korth et al. | |

FOREIGN PATENT DOCUMENTS

| | | |
|---|---|---|
| CN | 102007135 A | 4/2011 |
| JP | 8-311078 A | 11/1996 |
| JP | 2007-51146 A | 3/2007 |
| JP | 2008-169157 A | 7/2008 |
| WO | WO 2008/084885 A1 | 7/2008 |
| WO | WO 2009/104766 A1 | 8/2009 |

OTHER PUBLICATIONS

I. P. Urtane et al., "Synthese der Cyclischen Siliciumorganischen Ester von Diethanolaminen", Zeitschrift fuer Anorganische und Allgemeine Chemie, 1985, pp. 179-195, vol. 520.
M. G. Voronkov et al., Carbo-Functionally Substitute 1, 3-Dioxa-6-aza-2-Silacyclooctanes, Zhurnal Obshchei Khimii, 1985, pp. 1038-1041, vol. 55, No. 5.
M. G. Voronkov et al., "Synthesis and UV Spectra of 8-Mercaptoquinoline Organosilicon Derivatives and their Metal Halides Complexes", Journal of Organometallic Chemistry, 2002, pp. 91-96, vol. 642, No. 1-2.
Chinese Office Action dated Aug. 30, 2013 from the State Intellectual Property Office of P.R. China issued in Chinese Patent Application No. 201080031492.0.
Japanese Office Action issued in Japanese Application No. 2009-122322, dated Oct. 29, 2013.
Chinese Office Action Issued Jan. 28, 2014 by Chinese Patent Office in corresponding Chinese application No. 201080031492.0.

* cited by examiner

Primary Examiner — John Uselding
(74) Attorney, Agent, or Firm — Sughrue Mion, PLLC

(57) ABSTRACT

This invention relates to an organosilicon compound having a cyclic structure with nitrogen atom and silicon atom, and one or more sulfur atoms in its molecule, and having a bonding side of one or more groups having as small steric hindrance to silicon atom, a rubber composition formed by compounding an inorganic filler (B) and the organosilicon compound (C) into a rubber component (A) consisting of natural rubber and/or diene-based synthetic rubber, and a tire using such a rubber composition.

14 Claims, No Drawings

ORGANOSILICON COMPOUND AS WELL AS RUBBER COMPOSITION, TIRE PRIMER COMPOSITION, PAINT COMPOSITION AND ADHESIVE USING THE SAME

CROSS REFERENCE TO RELATED APPLICATIONS

This application is a National Stage of International Application No. PCT/JP2010/002933 filed on Apr. 22, 2010, which claims priority from Japanese Patent Application No. 2009-122322, filed on May 20, 2009, the contents of all of which are incorporated herein by reference in their entirety.

TECHNICAL FIELD

This invention relates to an organosilicon compound, and a rubber composition, primer composition, paint composition and adhesive containing such an organosilicon compound as well as a tire using such a rubber composition, and more particularly to an organosilicon compound capable of reducing a hysteresis loss of a rubber composition but also improving a wear resistance.

RELATED ART

Recently, it is demanded to improve the safeness of the tire on wet road surface from a viewpoint of the safeness of vehicles. Also, it is demanded to more reduce fuel consumption of the vehicle from a viewpoint of the reduction of carbon dioxide emissions associated with escalation in interest of environment concerns.

As to these demands, it has hitherto been known that a way of using an inorganic filler such as silica or the like as a filler in a rubber composition for use in a tire tread is effective as a technique of establishing the improvement of tire performances on wet road surface and the reduction of rolling resistance. Although the rubber composition compounded with the inorganic filler such as silica or the like reduces the rolling resistance of the tire and improves not only the braking performance on wet road surface but also the steering stability, there is a problem in the workability because the uncured viscosity is high and multistage milling and the like are required. In the rubber composition compounded with the inorganic filler such as silica or the like, therefore, the strength at break and wear resistance are largely deteriorated and there are caused problems such as curing retardation, poor dispersion of filler and so on.

When the inorganic filler such as silica or the like is compounded into the rubber composition for tread, it is essential to add a silane coupling agent for lowering the uncured viscosity of the rubber composition and ensuring the modulus of elasticity and wear resistance and more reducing the hysteresis loss. Also, this silane coupling agent is widely used in applications other than the rubber composition such as a primer composition, a paint composition, an adhesive and so on.

PRIOR ART ARTICLES

Patent Document

Patent Document 1: U.S. Pat. No. 3,842,111
Patent Document 2: U.S. Pat. No. 3,873,489

SUMMARY OF THE INVENTION

Problems to be Solved by the Invention

However, since the silane coupling agent is expensive, the compounding cost rises due to the compounding of the silane coupling agent. Also, the addition of a dispersion improving agent lowers the uncured viscosity of the rubber composition and improves the workability, but deteriorates the wear resistance. Further, when the dispersion improving agent is a compound having a high ionicity, the deterioration of the processability such as adhesion to roll or the like is observed. As a result of the inventors' examinations, it has been confirmed that even if the silane coupling agent is added while the inorganic filler such as silica or the like is compounded as a filler, the reduction of hysteresis loss and improvement of wear resistance in the rubber composition can not be obtained in a sufficiently satisfactory level and there is still a room for improvement. Also, it has been understood that although the silane coupling agent is used in the primer composition, paint composition, adhesive and the like as mentioned above, when an adherend is a hybrid material made from an organic material and an inorganic material, the adhesiveness and affinity at the interface between the organic material and the inorganic material are not sufficient in the primer composition, paint composition and adhesive using the conventional silane coupling agent and hence there is still a room for improvement.

It is, therefore, an object of the invention to solve the above problems of the conventional techniques and to provide a novel compound capable of largely reducing the hysteresis loss of the rubber composition but also highly improving the wear resistance. It is another object of the invention to provide a rubber composition, a primer composition, a paint composition and an adhesive containing such a compound as well as a tire using such a rubber composition.

Means for Solving Problems

The inventors have made various studies in order to achieve the above objects and found that since an organosilicon compound having a cyclic structure with nitrogen atom (N) and silicon atom (Si), and one or more sulfur atoms (S) in its molecule, and having a bonding site of one or more groups having a small steric hindrance to silicon atom (Si) is high in the reaction rate with an inorganic filler such as silica or the like, when such an organosilicon compound is compounded into a rubber component together with the inorganic filler, the efficiency of the coupling reaction is improved to highly improve the wear resistance while largely reducing the hysteresis loss of the rubber composition and further the organosilicon compound has an effect of improving the adhesiveness and affinity at an interface of a hybrid material made from an organic material and an inorganic material, and as a result the invention has been accomplished.

That is, the organosilicon compound of the invention is characterized by having a cyclic structure with nitrogen atom (N) and silicon atom (Si), and one or more sulfur atoms (S) in its molecule, and having a bonding site of one or more groups having a small steric hindrance to silicon atom (Si).

In a preferable embodiment of the organosilicon compound of the invention, the group having a small steris hindrance is at least one selected from the group consisting of hydrogen atom, methyl group and hydroxyl group.

The organosilicon compound of the invention is preferable to be an organosilicon compound represented by the following general formula (I):

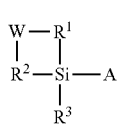 (I)

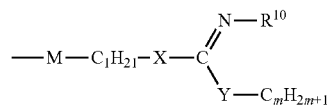 (VII)

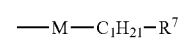 (VIII)

[wherein A is a group containing sulfur atom (S) and reacting with a rubber component;

W is represented by —$NR^4$—, —O— or —$CR^4R^5$— (wherein $R^5$ is —$R^6$ or —$C_mH_{2m}$—$R^7$, provided that $R^7$ is —$NR^4R^6$, —$NR^4$—$NR^4R^6$ or —N=$NR^4$, and $R^4$ is —$C_nH_{2n+1}$ and $R^6$ is —$C_qH_{2q+1}$, and m, n and q are independently 0-20);

$R^1$ and $R^2$ are independently -M-$C_lH_{2l}$— (wherein M is —O— or —$CH_2$— and l is 0-10) provided that M in one or more of $R^1$ and $R^2$ is —O—;

$R^3$ is a hydrogen atom, methyl group or hydroxyl group].

The group containing sulfur atom (S) and reacting with the rubber component is preferable to contain at least one selected from the group consisting of polysulfide group, thioester group, thiol group, dithiocarbonate group, dithioacetal group, hemithioacetal group, vinylthio group, α-thiocarbonyl group, β-thiocarbony group, S—CO—$CH_2$—O moiety, S—CO—CO moiety and S—$CH_2$—Si moiety, and is particularly preferable to contain at least one of polysulfide group and thioester group.

Also, A in the general formula (I) is preferable to be represented by the following general formula (II), (III) or (IV):

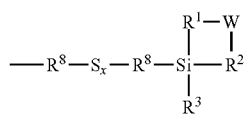 (II)

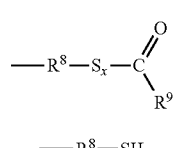 (III)

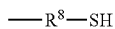 (IV)

[wherein W, $R^1$, $R^2$ and $R^3$ in the formula (II) have the same meanings as mentioned above;

$R^8$ in the formulae (II), (III) and (IV) is represented by the following general formula (V) or (VI):

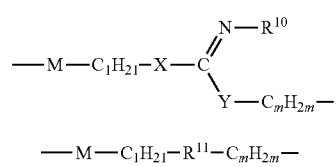 (V), (VI)

(wherein M, l and m have the same meanings as mentioned above, X and Y are independently —O—, —$NR^4$— or —$CH_2$— and $R^{10}$ is —$OR^4$, —$NR^4R^6$ or —$R^4$, and $R^{11}$ is —$NR^4$—, —$NR^4$—$NR^4$— or —N=N—, provided that $R^4$ and $R^5$ have the same meanings as mentioned above) or by -M-$C_lH_{2l}$— (wherein M and l have the same meanings as mentioned above);

$R^9$ in the formula (III) is represented by the following general formula (VII) or (VIII):

(wherein M, X, Y, $R^{10}$, $R^7$, l and m have the same meanings as mentioned above) or by —$C_l$—$H_{2l}$—$R^{12}$ (wherein $R^{12}$ is —$NR^4R^6$, —$NR^4$—$NR^4R^6$, —N=$NR^4$ or -M-$C_mH_{2m+1}$ or an aromatic hydrocarbon group having a carbon number of 6-20, provided that $R^4$, $R^6$, M, l and m have the same meanings as mentioned above);

x in the formulae (II) and (III) is 1-10].

In the above preferable organosilicon compound, M is preferable to be —O—.

In the organosilicon compound of the general formula (I), it is preferable that W is represented by —$NR^4$— (wherein $R^4$ has the same meaning as mentioned above), $R^1$ and $R^2$ are independently represented by —O—$C_lH_{2l}$— (wherein l has the same meaning as mentioned above), $R^3$ is a hydrogen atom, methyl group or hydroxyl group, $R^8$ is represented by —$C_lH_{2l}$— (wherein l has the same meaning as mentioned above), $R^9$ is a linear or branched alkyl group represented by —$C_lH_{2l+1}$ (wherein l has the same meaning as mentioned above) or an aromatic hydrocarbon group having a carbon number of 6-20.

In the organosilicon compound of the general formula (I), it is preferable that W is represented by —O— or —$CR^4R^6$— (wherein $R^4$ and $R^6$ have the same meanings as mentioned above), $R^1$ and $R^2$ are independently represented by —O—$C_lH_{2l}$— (wherein l has the same meaning as mentioned above), $R^3$ is a hydrogen atom, methyl group or hydroxyl group, $R^8$ is represented by —$C_lH_{2l}$— (wherein l has the same meaning a mentioned above), $R^9$ is represented by —$C_lH_{2l+1}$ (wherein l has the same meaning as mentioned above).

Also, the rubber composition of the invention is characterized in that an inorganic filler (B) and the above organosilicon compound (C) are compounded into a rubber component (A) consisting of natural rubber and/or diene-based synthetic rubber.

The rubber composition of the invention is preferable that 5-140 parts by mass of the inorganic filler (B) is compounded based on 100 parts by mass of the rubber component (A) consisting of natural rubber and/or diene-based synthetic rubber; and the organosilicon compound (C) is included in an amount of 1-20 mass % of the compounding amount of the inorganic filler (B).

In a preferable embodiment of the rubber composition of the invention, the inorganic filler (B) is silica or aluminum hydroxide. The silica is preferable to have a BET surface area of 40-350 $m^2/g$.

Also, the tire of the invention is characterized by using the above rubber composition.

Furthermore, the primer composition of the invention is characterized by containing the above organosilicon compound. The paint composition of the invention is characterized by using the above organosilicon compound. The adhesive of the invention is characterized by using the above organosilicon compound.

Effect of the Invention

According to the invention, there can be provided an organosilicon compound having a cyclic structure with nitrogen atom (N) and silicon atom (Si), sulfur atom (S) and a bonding site of the group having a small steric hindrance to silicon atom (Si) and capable of largely reducing the hysteresis loss of the rubber composition and highly improving the wear resistance. Also, there can be provided a rubber composition containing such an organosilicon compound and a tire using such a rubber composition and further a primer composition, paint composition and adhesive containing such an organosilicon compound.

EMBODIMENTS FOR CARRYING OUT THE INVENTION

<Organosilicon Compound>

The invention will be described in detail below. The organosilicon compound of the invention is characterized by having a cyclic structure with nitrogen atom (N) and silicon atom (Si), and one or more sulfur atoms (S) in its molecule, and having a bonding site of one or more groups having a small steric hindrance to silicon atom (Si). The organosilicon compound of the invention has a cyclic structure with nitrogen atom (N) and silicon atom (Si) and is stable even if the cyclic structure includes silicon-oxygen bond (Si—O). Therefore, there is no formation of alcohol component through hydrolysis of silicon-oxygen bond (Si—O), and a gas of a volatile organic compound (VOC) can be reduced in use.

Also, the organosilicon compound of the invention contains a nitrogen-containing functional group such as amino group, imino group, substituted amino group, substituted imino group or the like having a high affinity with a surface of an inorganic filler such as silica or the like, so that non-conjugated electron pair of nitrogen atom can be involved in the reaction of the organosilicon compound and the inorganic filler, and the coupling reaction rate is fast. However, when the cyclic structure with nitrogen atom (N) and silicon atom (Si) is a bicyclic structure, steric hindrance around silicon atom (Si) is large, so that the reactivity with the inorganic filler is low and the coupling efficiency largely lowers. On the contrary, the organosilicon compound of the invention has a bonding site of one or more groups having a small steric hindrance to silicon atom (Si), so that the reactivity with the inorganic filler such as silica or the like is high. Therefore, when the organosilicon compound of the invention is added to the inorganic filler compounded rubber composition instead of the conventional silane coupling agent, the coupling efficiency is improved and hence it is possible to highly improve the wear resistance while largely reducing the hysteresis loss of the rubber composition. Also, the organosilicon compound of the invention is high in the addition efficiency, so that the high effect is obtained even in the small amount, which contributes to the reduction of the compounding cost.

In the invention, hydrogen atom (—H), methyl group (—CH$_3$) and hydroxyl group (—OH) are preferable as the group having a small steric hindrance. When hydrogen atom, methyl group or hydroxyl group is bonded to silicon atom (Si), the reactivity of the organosilicon compound with the inorganic filler is particularly high, and the coupling efficiency can be improved highly. Also, the organosilicon compound of the invention is preferable to have 1-6 silicon-oxygen bonds (Si—O). When the organosilicon compound includes 1-6 silicon-oxygen bonds (Si—O), the reactivity with the inorganic filler such as silica or the like is high, and the coupling efficiency is further improved.

The organosilicon compound of the invention is preferable to be a compound represented by the general formula (I). The organosilicon compounds may be used alone or in a combination of two or more.

<<Compounds of Formula (I)>>

In the general formula (I), A is a group containing sulfur atom (S) and reacting with a rubber component (polymer). The organosilicon compound represented at its cyclic structure moiety by the formula (I) reacts with the inorganic filler such as silica or the like, so that the coupling ability with the rubber component and the inorganic filler is obtained by further providing the group reacting with the rubber component in the molecule. The group containing sulfur atom (S) and reacting with the rubber component (polymer) is preferable to contain at least one selected from the group consisting of polysulfide group, thioester group, thiol group, dithiocarbonate group, dithioacetal group, hemithioacetal group, vinylthio group, α-thiocarbonyl group, β-thiocarbonyl group, S—CO—CH2—O moiety, S—CO—CO moiety (thiodiketone group) and S—CH2—Si moiety. It is particularly preferable to contain at least one of polysulfide group and thioester group.

In the general formula (I), W is represented by —NR$^4$—, —O— or —CR$^4$R$^5$—, wherein R$^5$ is —R$^6$ or —C$_m$H$_{2m}$—R$^7$, and R$^7$ is —NR$^4$R$^6$, —NR$^4$—NR$^4$R$_6$ or —N=NR$_4$, and R4 is —C$_n$H$_{2n+1}$, and R$^6$ is —C$_q$H$_{2q+1}$, and m, n and q are independently 0-20, preferably 0-10. Moreover, —C$_m$H$_{2m}$— is a single bond or an alkylene group having a carbon number of 1-20 because m is 0-20. As the alkylene group having a carbon number of 1-20 are mentioned methylene group, ethylene group, trimethylene group, propylene group, tetramethylene group, hexamethylene group, octamethylene group, decamethylene group, dodecamethylene group, tetradecamethylene group, hexadecamethylene group, octadecamethylene group and so on. The alkylene group may be linear or branched. Also, —C$_n$H$_{2n+1}$ and —C$_q$H$_{2q+1}$ are hydrogen or an alkyl group having a carbon number of 1-20 because n and q are 0-20. As the alkyl group having a carbon number of 1-20 are mentioned methyl group, ethyl group, propyl group, butyl group, pentyl group, hexyl group, heptyl group, octyl group, decyl group, dodecy group, tridecyl group, tetradecyl group, pentadecyl group, hexadecyl group, heptadecyl group, steary group and so on. The alkyl group may be linear or branched.

In the general formula (I), R$^1$ and R$^2$ are independently represented by -M-C$_1$H$_{2l}$—, wherein M is —O— or —CH$_2$— and l is 0-10, provided that M in one or more of R$^1$ and R$^2$ is —O—. Moreover, —C$_1$H$_{2l}$— is a single bond or an alkylene group having a carbon number of 1-10 because l is 0-10. As the alkylene group having a carbon number of 1-10 are mentioned methylene group, ethylene group, trimethylene group, propylene group and so on. The alkylene group may be linear or branched.

In the general formula (I), R$^3$ is hydrogen atom, methyl group or hydroxyl group. R$^3$ is small in the steric hindrance and largely contributes to improve the coupling reaction between the rubber component and the inorganic filler.

In the general formula (I), A is preferable to be represented by the general formula (II), (III) or (IV). Here, W, R$^1$, R$^2$ and R$^3$ in the formula (II) have the same meanings as mentioned above, and R$^8$ in the formulae (II), (III) and (IV) is represented by the general formula (V) or (VI) or -M-C$_1$H$_{2l}$—, and R$^9$ in the formula (III) is represented by the general formula (VII) or (VIII) or —C$_1$H$_{2l}$—R$^{12}$, and x in the formulae (II)

and (III) is 1-10, preferably 2-4. M is —O— or —CH$_2$—, and l is 0-10. Moreover, —C$_l$H$_{2l}$— is the same as mentioned above.

In the formulae (V) and (VI), M is —O— or —CH$_2$—, and l and m are 0-10. In the formula (V), X and Y are independently —O—, —NR$_4$— or —CH$_2$—, and R$^{10}$ is —OR$^4$, —NR$^4$R$^6$ or —NR$^4$, wherein R$^4$ is —C$_n$H$_{2n+1}$ and R$^6$ is —C$_q$H$_{2q+1}$. In the formula (VI), R$^{11}$ is —NR$^4$—, —NR$^4$—NR$^4$— or —N=N—, wherein R$^4$ is —C$_n$H$_{2n+1}$. Moreover, —C$_n$H$_{2n+1}$ and —C$_q$H$_{2q+1}$ are the same as mentioned above.

Also, R$^9$ in the formula (III) is represented by the general formula (VII) or (VIII) or —C$_l$H$_{2l}$—R$^{12}$, and is particularly preferable to be represented by —C$_l$H$_{2l+1}$, provided that M, X, Y, R$^{12}$, R$^7$, l and m have the same meanings as mentioned above. R$^{12}$ is —NR$^4$R$^6$, —NR$^4$—NR$^4$R$^6$, —N=NR$^4$ or -M-C$_m$H$_{2m+1}$, provided that R$^4$, R$^6$, M, l and m have the same meanings as mentioned above. Moreover, —C$_l$H$_{2l}$— is the same as mentioned above. Also, —C$_m$H$_{2m+1}$ is hydrogen or an alkyl group having a carbon number of 1-20 because m is 0-20. As the alkyl group having a carbon number of 1-20 are mentioned methyl group, ethyl group, propyl group, butyl group, pentyl group, hexyl group, heptyl group, octyl group, decyl group, dodecyl group, tridecyl group, tetradecyl group, pentadecyl group, hexadecyl group, heptadecyl group, sterayl group and so on. The alkyl group may be linear or branched. As the aromatic hydrocarbon group having a carbon number of 6-20 are mentioned aryl groups such as phenyl group, tolyl group, xylyl group, cumenyl group, naphthylene group and the like, and aralkyl groups such as benzyl group, phenethyl group and the like.

In the compound of the formula (I), M is preferable to be —O— (oxygen). In this case, the reactivity with the inorganic filler such as silica or the like is higher as compared with the compound wherein M is —CH$_2$—.

When W is represented by —NR$^4$—, R$^1$ and R$^2$ are preferable to be independently represented by —O—C$_l$H$_{2l}$—, and R$^3$ is hydrogen atom, methyl group or hydroxyl group, and R$^8$ is preferably represented by C$_l$H$_{2l}$—, and R$^9$ is preferable to be a linear or branched alkyl group represented by —C$_l$H$_{2l+1}$ or an aromatic hydrocarbon group having a carbon number of 6-20.

On the other hand, when W is represented by —O— or —CR$^4$R$^6$—, R$^1$ and R$^2$ are preferable to be independently represented by —O—C$_l$H$_{21}$—, and R$^3$ is hydrogen atom, methyl group or hydroxyl group, and R$^8$ is preferably represented by —C$_l$H$_{2l}$—, and R$^9$ is preferably represented by —C$_l$H$_{2l+1}$.

<<Synthesis of Organosilicon Compound>>

The organosilicon compound of the invention can be synthesized, for example, by adding an amine compound such as N-methyl diethanolamine, N-ethyl diethanolamine or the like to a compound represented by (C$_l$H$_{2l+1}$O)$_2$R$^3$Si-A [wherein l, R$^3$ and A have the same meanings as mentioned above] and further adding an acid such as p-toluenesulfonic acid, hydrochloric acid or the like or a titanium alkoxide such as titanium tetra-n-butoxide or the like as a catalyst and then heating to substitute two C$_l$H$_{2l+1}$— groups with a bivalent group represented by —R$^1$—W—R$^2$—.

<<Concrete Example of Organosilicon Compound>>

As the organosilicon compound of the invention are concretely mentioned 3-octanoylthio-propyl(methyl)1,3-dioxa-6-methylaza-2-silacyclooctane, bis(3-(methyl)1,3-dioxa-6-methylaza-2-silacyclooctyl-propyl)disulfide, 3-octanoylthio-propyl(hydroxy)1,3-dioxa-6-methylaza-2-silacyclooctane, bis(3-(hydroxy)1,3-dioxa-6-methylaza-2-silacyclooctyl-propyl)disulfide, 3-octanoylthio-propyl(hydro)1,3-dioxa-6-methylaza-2-silacyclooctane, bis(3-(hydro)1,3-dioza-6-methylaza-2-silacyclooctyl-propyl)disulfide, 3-octanoylthio-propyl(methyl)1,3-dioxa-6-butylaza-2-silacyclooctane, bis(3-(methyl)1,3-dioxa-6-butylaza-2-silacyclooctyl-propyl)disulfide, 3-octanoylthio-propyl(hydroxy)1,3-dioxa-6-butylaza-2-silacyclooctane, bis(3-(hydroxy)1,3-dioxa-6-butylaza-2-silacyclooctyl-propyl)disulfide, 3-octnoylthio-propyl(hydro)1,3-dioxa-6-butylaza-2-silacyclooctane, bis(3-(hydro)1,3-dioxa-6-butylaza-2-silacyclooctyl-propyl)disulfide, 3-octanoylthio-propyl(methyl)1,3-dioxa-6-dodecylaza-2-silacyclooctane, 3-octanoylthio-propyl(methyl)1,3-dioxa-6-pentadecylaza-2-silacyclooctane, 3-octanoylthio-propyl(methyl)1,3-dioxa-6-octadecylaza-2-silacyclooctane, 3-octanoylthio-propyl(hydroxy)1,3-dioxa-6-dodecylaza-2-silacyclooctane, 3-octanoylthio-propyl(hydroxy)1,3-dioxa-6-pentadecylaza-2-silacycloocatne, 3-octanoylthio-propyl(hydrox)1,3-dioxa-6-octadecylaza-2-silacyclooctane, 3-octanoylthio-propyl(hydroxy)1,3-dioxa-6-deodecylaza-2-silacyclooctane, 3-octanoylthio-propyl(hydro)1,3-dioxa-6-pentadecylaza-2-silacyclooctane, 3-octanoylthio-propyl(hydro)1,3-dioxa-6-octadecylaza-2-silacyloocatane, 3-ethanoylthio-propyl(methyl)1,3-dioxa-6-dodecyaza-2-silacyclooctane, 3-ethanoylthio-propyl(methyl)1,3-dioxa-6-pentadecylaza-2-silacyclooctane, 3-ethanoylthio-propyl(methyl)1,3-dioxa-6-octadecylaza-2-silacyclooctane, 3-ethanoylthio-propyl(hydroxy)1,3-dioxa-6-dodecylaza-2-silacyclooctane, 3-ethanoylthio-propyl(hydroxy)1,3-dioxa-6-pentadecylaza-2-silacyclooctane, 3-ethanoylthio-propyl(hydroxy)1,3-dioxa-6-octadecylaza-2-silacyclooctane, 3-ethanoylthio-propyl(hydro)1,3-dioxa-6-dodecylaza-2-silacyclooctane, 3-ethanoylthio-propyl(hydro)1,3-dioxa-6-pentadecylaza-2-silacyclooctane, 3-ethanoylthio-propyl(hydro)1,3-dioxa-6-octadecylaza-2-silacyclooctane, 3-pentanoylthio-propyl(methyl)1,3-dioxa-6-dodecyaza-2-silacyclooctane, 3-pentanoylthio-propyl(methyl)1,3-dioxa-6-pentadecylaza-2-silacyclooctane, 3-pentanoylthio-propyl(methyl)1,3-dioxa-6-octadecylaza-2-silacyclooctane, 3-pentanoylthio-propyl(hydroxy)1,3-dioxa-6-dodecylaza-2-silacyclooctane, 3-pentanoylthio-propyl(hydroxy)1,3-dioxa-pentadecylaza-2-silacyclooctane, 3-pentanoylthio-propyl(hydroxy)1,3-dioxa-6-octadecylaza-2-silacyclooctane, 3-pentanoylthio-propyl(hydro)1,3-dioxa-6-dodecylaza-2-silacyclooctane, 3-pentanoylthio-propyl(hydro)1,3-dioxa-6-pentadecylaza-2-silacyclooctane, 3-pentanoylthio-propyl(hydro)1,3-dioxa-6-octadecylaza-2-silacyclooctane, 3-dodecanoylthio-propyl(methyl)1,3-dioxa-6-dodecylaza-2-silacyclooctane, 3-dodecanoylthio-propyl(methyl)1,3-dioxa-6-pentadecylaza-2-silacyclooctane, 3-dodecanoylthio-propyl(methyl)1,3-dioxa-6-octadecylaza-2-silacyclooctane, 3-dodecanoylthio-propyl(hydroxy)1,3-dioxa-6-dodecylaza-2-silacyclooctane, 3-dodecanoylthio-propyl(hydroxy)1,3-dioxa-6-pentadecylaza-2-silacyclooctane, 3-dodecanoylthio-propyl(hydroxy)1,3-dioxa-6-octadecylaza-2-silacyclooctane, 3-dodecanoylthio-propyl(hydro)1,3-dioxa-dodecylaza-2-silacyclooctane, 3-dodecanoylthio-propyl(hydro)1,3-dioxa-6-pentadecylaza-2-silacyclooctane, 3-dodecanoylthio-propyl(hydro)1,3-dioxa-6-octadecylaza-2-silacyclooctane, 3-hexadecanoylthio-propyl(methyl)1,3-dioxa-6-dodecylaza-2-silacyclooctane, 3-hexadecanoylthio-propyl(methyl)1,3-dioxa-6-pentadecylaza-2-silacyclooctane, 3-hexadecanoylthio-propyl(methyl)1,3-dioxa-6-octadecylaza-2-silacyclooctane, 3-hexadecanoylthio-propyl(hydroxy)1,3-dioxa-6-dodecylaza-2-silacycloocatne, 3-hexadecanoylthio-propyl(hydroxy)1,3-dioxa-6-pentadecylaza-2-silacycloocatne, 3-hexadecanoylthio-propyl(hydroxy)1,3-dioxa-6-octadecylaza-2-silacyclooctane, 3-hexadecanoylthio-propyl(hydro)1,3-dioxa-6-dodecylaza-2-silacyclooctane, 3-hexadecanoylthio-propyl(hydro)1,3-dioxa-6-pentadecylaza-2-silacyclooctane, 3-hexadecanoylthio-propyl(hydro)1,3-dioxa-6-octadecylaza-2-silacyclooctane, bis(3-(methyl)1,3-dioxa-6-dodecylaza-2-silacyclooctyl-propyl)disulfide, bis(3-(methyl)1,3-dioxa-6-tridecylaza-2-silacyclooctyl-propyl)disulfide, bis(3-(methyl)1,3-dioxa-6-tetradecylaza-2-silacyclooctyl-propyl)disulfide, bis(3-(methyl)1,3-d-oxa-6-pentadecylaza-2-silacyclooctyl-propyl)disulfide, bis(3-(methyl)1,3-dioxa-6-hexadecylaza-2-silacyclooctyl-propyl)disulfide, bis(3-(methyl)1,3-dioxa-6-octadecylaza-2-silacyclooctyl-propyl)disulfide, bis(3-(methyl)1,3-dioxa-6-nonadecylaza-2-silacyclooctyl-propyl)disulfide, bis(3-(methyl)1,3-dioxa-6-eicocylaza-2-silacyclooctyl-propy)disulfide, bis(3-(hydroxy)1,3-dioxa-6-dodecylaza-2-silacyclooctyl-propyl)disulfide, bis(3-(hydroxy)1,3-dioxa-6-tridecylaza-2-silacyclooctyl-propyl)disulfide, bis(3-(hydroxy)1,3-dioxa-6-tetradecylaza-2-silacyclooctyl-propyl)disulfide, bis(3-(hydroxy)1,3-dioxa-6-pentadecylaza-2-silacyclooctyl-propyl)disulfide, bis(3-(hydroxy)1,3-dioxa-6-hexadecylaza-2-silacyclooctyl-propyl)disulfide, bis(3-(hydroxy)1,3-dioxa-6-octadecylaza-2-silacyclooctyl-propyl)disulfide, bis(3-hydroxy)1,3-dioxa-6-nonadecylaza-2-silacyclooctyl-propyl)disulfide, bis(3-(hydroxy)1,3-dioxa-6-eicocylaza-2-silacyclooctyl-propyl)disulfide, bis(3-(hydro)1,3-dioxa-6-dodecylaza-2-silacyclooctyl-propyl)disulfide, bis(3-(hydro)1,3-dioxa-6-tridecylaza-2-silacyclooctyl-propyl)disulfide, bis(3-(hydro)1,3-dioxa-6-tetradecylaza-2-silacyclooctyl-propyl)disulfide, bis(3-(hydro)1,3-dioxa-6-pentadecylaza-2-silacyclooctyl-propeyl)disulfide, bis(3-(hydro)1,3-dioxa-6-hexadecylaza-2-silacyclooctyl-propyl)disulfide, bis(3-(hydro)1,3-dioxa-6-octadecylaza-2-silacyclooctyl-propyl)disulfide, bis(3-(hydro)1,3-dioxa-6-nonadecylaza-2-silacyclooctyl-propyl)disulfide, bis(3-(hydro)1,3-dioxa-6-eicocylaza-2-silacyclooctyl-propyl)disulfide, bis(3-(methyl)1,3-dioxa-6-dodecylaza-2-silacyclooctyl-propyl)tetrasulfide, bis(3-(methyl)1,3-dioxa-6-tridecylaza-2-silacyclooctyl-propyl)tetrasulfide, bis(3-(methyl)1,3-dioxa-6-tetradecylaza-2-silacyclooctyl-propyl)tetrasulfide, bis(3-(methyl)1,3-dioxa-6-pentadecylaza-2-silacyclooctyl-propyl)tetrasulfide, bis(3-(methyl)1,3-dioxa-6-hexadecylaza-2-silacyclooctyl-propyl)tetrasulfide, bis(3-(methyl)1,3-dioxa-6-octadecylaza-2-silacyclooctyl-propyl)tetrasulfide, bis(3-(methyl)1,3-dioxa-6-nondecylaza-2-silacycloocty-propyl)tetrasulfide, bis(3-(methyl)1,3-dioxa-6-eicocylaza-2-silacyclooctyl-propyl)tetrasulfide, bis(3-(hydroxy)1,3-dioxa-6-dodecylaza-2-silacyclooctyl-propyl)tetrasulfide, bis(3-(hydroxy)1,3-dioxa-6-tridecylaza-2-silacyclooctyl-propyl)tetrasuldife, bis(3-(hydroxy)1,3-dioxa-6-tetradecylaza-2-silacyclooctyl-propyl)tetrasulfide, bis(3-(hydroxy)1,3-dioxa-6-pentadecylaza-2-silacyclooctyl-propyl)tetrasulfide, bis(3-(hydroxy)1,3-dioxa-6-hexadecylaza-2-silacyclooctyl-propyl)tetrasulfide, bis(3-(hydroxy)1,3-dioxa-6-octadecylaza-2-silacyclooctyl-propyl)tetrasulfide, bis(3-(hydroxy)1,3-dioxa-6-nonadecylaza-2-silacyclooctyl-propyl)tetrasulfide, bis(3-(hydroxy)1,3-dioxa-6-eicocylaza-2-silacyclooctyl-propyl)tetrasulfide, bis(3-(hydro)1,3-dioxa-6-dodecylaza-2-silacyclooctyl-propy) tetrasuldife, bis(3-(hydro)1,3-dioxa-6-tridecylaza-2-silacyclooctyl-propyl)tetrasulfide, bis(3-(hydro)1,3-dioxa-6-tetradecylaza-2-silacyclooctyl-propyl)tetrasulfide, bis(3-(hydro)1,3-dioxa-6-pentadecylaza-2-silacyclooctyl-propyltetrasulfide, bis(3-(hydro)1,3-dioxa-6-hexadecylaza-2-silacyclooctyl-propyl)tetrasulfide, bis(3-(hydro)1,3-dioxa-6-octadecylaza-2-silacyclooctyl-propyl)tetrasulfide, bis(3-(hydro)1,3-dioxa-6-nonadecylaza-2-silacyclooctyl-propyl)tetrasulfide, bis(3-(hydro)1,3-dioxa-6-eicocylaza-2-silacyclooctyl-propyl) tetrasulfide, bis(3-(methyl)1,3-dioxa-6-dodecylaza-2-silacyclooctyl-propyl)trisulfide, bis(3-(methyl)1,3-dioxa-6-hexadecylaza-2-silacyclooctyl-propyl)trisulfide, bis(3-(methyl)1,3-dioxa-6-octadecylaza-2-silacyclooctyl-propyl)trisulfide, bis(3-(hydroxy)1,3-dioxa-6-dodecylaza-2-silacyclooctyl-propyl)trisulfide, bis(3-(hydroxy)1,3-dioxa-6-hexadecylaza-2-silacyclooctyl-propyl)trisulfide, bis(3-(hydroxy)1,3-dioxa-6-octadecylaza-2-silacyclooctyl-propryl)trisulfide, bis(3-(hydro)1,3-dioxa-6-dpdecylaza-2-silacyclooctyl-propyl)trisulfide, bis(3-(hydro)1,3-dioxa-6-hexadecylaza-2-silacyclooctyl-propyl)trisulfide, bis(3-(hydro)1,3-dioxa-6-octadecylaza-2-silacyclooctyl-propyl) trisulfide, (3-mercaptopropyl)(methyl) 1,3-dioxa-6-methylaza-2-silacyclooctane, (3-mercapropentyl)(methyl)1,3-dioxa-6-methylaza-2-silacyclooctane, (3-mercaptodecyl)(methyl)1,3-dioxa-6-methylaza-2-silacyclooctance, (3-mercaptopropyl)(methyl)1,3-dioxa-6-ethylaza-2-silacyclooctance, (3-mercaptopropyl)(methyl)1,3-dioxa-6-butylaza-2-silacyclooctane, (3-mercaptopropyl)(methyl)1,3-dioxa-6-decylaza-2-silacyclooctane, (3-mercaptopropyl)(methyl)1,3-dioxa-6-dodecylaza-2-silacyclooctane, (3-mercaptopropyl)(methyl)1,3-dioxa-6-octadecylaza-2-silacyclooctane, (3-mercaptopropyl)(methyl)1,3-dioxa-6-methylaza-silacyclooctane, (3-mercaptopentyl)(hydroxy)1,3-dioxa-6-methylaza-2-silacyclooctane, (3-mercaptodecyl)(hydroxy)1,3-dioxa-6-methylaza-2-silacyclooctane, (3-mercaptopropyl)(hydroxy)1,3-dioxa-6-ethylaza-2-silacyclooctane, (3-mercaptopropyl)(hydroxy)1,3-dioxa-6-butylaza-2-silacyclooctane, (3-mercaptopropyl)(hydroxy)1,3-dioxa-6-decylaza-2-silacyclooctane, (3-mercaptopropyl)(hydroxy)1,3-dioxa-6-dodecylaza-2-silacyclooctane, (3-mercaptopropyl)(hydroxy)1,3-dioxa-6-octadecylaza-2-silacyclooctane, (3-mercaptopropyl)(hydro)1,3-dioxa-6-methylaza-2-silacyclooctane, (3-mercaptopentyl)(hydro)1,3-dioxa-6-methylaza-2-silacyclooctane, (3-mercaptodecyl)(hydro)1,3-dioxa-6-methylaza-2-silacyclooctane, (3-mercaptopropyl)(hydro)1,3-dioxa-6-ethylaza-2-silacyclooctane, (3-mercaptopropyl)(hydro)1,3-dioxa-6-butylaza-2-silacyclooctane, (3-mercaptopropyl)(hydro)1,3-dioxa-6-decylaza-2-silacyclooctane, (3-mercaptopropyl)(hydro)1,3-dioxa-6-dodecylaza-2-silacyclooctane, (3-mercaptopropyl)(hydro)1,3-dioxa-6-octadecylaza-2-silacyclooctane and so on.

<Rubber Composition>

The rubber composition of the invention is characterized by compounding the inorganic filler (B) and the above organosilicon compound (C) into the rubber component (A) consisting of natural rubber and/or diene-based synthetic rubber. Preferably, 5-140 parts by mass of the inorganic filler (B) is compounded based on 100 parts by mass of the rubber component consisting of natural rubber and/or diene-based synthetic rubber, and further the organosilicon compound (C) is compounded in an amount of 1-20 mass % of the compounding amount of the inorganic filler (B).

When the content of the organosilicon compound (C) is less than 1 mass % of the compounding amount of the inorganic filler (B), the effect of reducing the hysteresis loss of the rubber composition and the effect of improving the wear resistance are insufficient, while when it exceeds 20 mass %, the effects are saturated.

The rubber component (A) in the rubber composition of the invention consists of natural rubber and/or diene-based synthetic rubber. As the diene-based synthetic rubber are mentioned styrene-butadiene copolymer rubber (SBR), polybutadiene rubber (BR), polyisoprene rubber (IR), butyl rubber (IIR), ethylene-propylene copolymer and so on. Moreover, the rubber component (A) is preferable to contain carbon-carbon double bond in its molecule for reacting with the organosilicon compound (C). These rubber components may be used alone or in a blend of two or more.

As the inorganic filler (B) used in the rubber composition of the invention are mentioned silica, aluminum hydroxide, alumina, clay, calcium carbonate and so on. Among them, silica and aluminum hydroxide are preferable, and silica is particularly preferable from a viewpoint of the reinforcing property. When the inorganic filler (B) is silica, since the organosilicon compound (C) has a functional group having a high affinity with silanol group on the surface of silica and/or a functional group having a high affinity with silicon atom (Si), the coupling efficiency is highly improved, and the effect of reducing the hysteresis loss of the rubber composition and improving the wear resistance becomes more remarkable. Moreover, silica is not particularly limited, and wet type silica (hydrous silicic acid), dry type silica (anhydrous silicic acid) and the like may be used. On the other hand, as aluminum hydroxide is preferably used HIGILITE (registered trade mark, made by Showa Denko Co., Ltd.).

The silica is preferable to have a BET surface area of 40-350 $m^2/g$.

When the BET surface area of silica is less than 40 $m^2/g$, the particle size of silica is too large, and the wear resistance is largely deteriorated, while when the BET surface area of silica exceeds 350 $m^2/g$, the particle size of silica is too small, and the hysteresis loss is largely increased.

The compounding amount of the inorganic filler (B) is preferable to be 5-140 parts by mass based on 100 parts by mass of the rubber component (A). When the compounding amount of the inorganic filler (B) is less than 5 parts by mass based on 100 parts by mass of the rubber component (A), the effect of reducing the hysteresis loss is insufficient, while when it exceeds 140 parts by mass, the workability is considerably deteriorated.

In addition to the above rubber component (A), inorganic filler (B) and organosilicon compound (C), the rubber composition of the invention may be properly compounded with additives usually used in the rubber industry such as carbon black, softening agent, vulcanizing agent, vulcanization accelerator, antioxidant, zinc white, stearic acid and the like in accordance with the use purpose. As such additives may be preferably used commercially available ones. Moreover, the rubber composition of the invention may be prepared by compounding the rubber component (A) with the inorganic filler (B) and organosilicon compound (C) and, if necessary, various additives properly selected, and then milling and warming up them and extruding and the like.

<Tire>

Also, the tire of the invention is characterized by using the aforementioned rubber composition. The rubber composition is preferable to be used in a tread. In the tire of the invention, the rolling resistance is largely reduced, and further the wear resistance is highly improved. Moreover, the tire of the invention has the conventionally known structure without being particularly limited, and can be manufactured by the usual method. Also, when the tire of the invention is a pneumatic tire, an inert gas such as nitrogen, argon, helium or the like may be used in addition to usual air or air having an adjusted partial oxygen pressure as a gas to be filled in the tire.

<Primer Composition, Paint Composition and Adhesive>

Further, the primer composition of the invention is characterized by containing the organosilicon compound, and the paint composition of the invention is characterized by containing the organosilicon compound, and the adhesive of the invention is characterized by containing the organosilicon compound. Since the aforementioned organosilicon compound of the invention has a high affinity even with hydroxy group other than silanol group, the reaction with a variety of inorganic compounds having hydroxy group can be promoted, and there is an effect of improving the adhesiveness at the interface with a hybrid material made of an organic material and an inorganic material and the affinity. Therefore, the primer composition, paint composition and adhesive including the above organosilicon compound can improve the adhesiveness and affinity with the interface between the organic material and the inorganic material.

The primer composition of the invention may contain a catalyst made from a metal such as tin, titanium or the like or a metal compound as a curing acceleration component in addition to the organosilicon compound. Also, an organic solvent may be included for adjusting the viscosity of the primer composition. The paint composition of the invention may contain a pigment, metal particles, resin and further organic solvent or water in addition to the organosilicon compound. The adhesive of the invention may contain a resin and further an organic solvent for adjusting the viscosity of the adhesive in addition to the organosilicon compound. Moreover, each of the primer composition, paint composition and adhesive of the invention may be prepared by mixing the organosilicon compound with additives and solvent properly selected in accordance with the use purpose according to the well-known method.

EXAMPLES

The invention will be described in more detail with reference to the following examples. The invention is not limited by these examples.

Production Example 1 of Organosilicon Compound

In a four-necked flask of 500 mL are weighed 60 g of 3-octanoylthio-propyldiethoxymethyl silane, 20 g (1.02 eq) of N-methyldiethanol amine, 0.8 g of titanium tetra-n-butoxide and 220 mL of toluene. The flask is heated in an oil bath while flowing dry nitrogen (0.2 L/min) with stirring by a mechanical stirrer and then a Dimroth condenser is attached to conduct reflux for 11 hours. Thereafter, the solvent is removed by a rotary evaporator at 20 hPa/40° C., and subsequently the remaining volatile matter is removed by a rotary pump (10 Pa) and a cold trap (dry ice+ethanol) to obtain 70 g of a yellow transparent liquid [organosilicon compound (C-1). It has been confirmed from analytical result of gas chromatography (GC) that the resulting liquid consists of 10% of a starting material and 90% of a target product. As analyzed by $^1$H-NMR, the resulting liquid is confirmed to have $^1$H-NMR (CDCl$_3$, 700 MHz, δ:ppm)=3.8 (m; 4H), 2.8 (t:2H), 2.5 (m; 6H), 2.4 (m; 3H), 1.6 (m; 4H), 1.3 (m; 8H), 0.8 (t; 3H), 0.7 (t; 2H) and 0.1 (s; 3H) and to be a compound of the formula (I) wherein A is the formula (III) and W is —N(CH$_3$)— and R$^1$ is —O—CH$_2$CH$_2$— (connected to Si at a side of O) and R$^2$ is —O—CH$_2$CH$_2$— (connected to Si at a side of O) and R$^3$ is —CH$_3$ and R$^8$ is —CH$_2$CH$_2$CH$_2$— and R$^9$ is —C$_7$H$_{15}$ and x is 1 [i.e. 3-octanoylthio-propyl(methyl) 1,3-dioxa-6-methylaza-2-silacyclooctane].

Production Example 2 of Organosilicon Compound

In a four-necked flask of 500 mL are weighed 40 g of bis(3-diethoxymethylsilylpropyl)disulfide, 20 g (1.02 eq) of N-methyldiethanol amine, 0.8 g of titanium tetra-n-butoxide and 220 mL of toluene. The flask is heated in an oil bath while flowing dry nitrogen (0.2 L/min) with stirring by a mechanical stirrer and then a Dimroth condenser is attached to conduct reflux for 11 hours. Thereafter, the solvent is removed by a rotary evaporator at 20 hPa/40° C., and subsequently the remaining volatile matter is removed by a rotary pump (10 Pa) and a cold trap (dry ice+ethanol) to obtain 50 g of a yellow transparent liquid [organosilicon compound (C-2). It has been confirmed from analytical result of gas chromatography (GC) that the resulting liquid consists of 10% of a starting material and 90% of a target product. As analyzed by $^1$H-NMR, the resulting liquid is confirmed to have $^1$H-NMR (CDCl$_3$, 700 MHz, δ:ppm)=3.8 (m; 8H), 2.7 (t:4H), 2.5 (m; 8H), 2.4 (m; 6H), 1.8 (m; 4H), 0.7 (t; 4H) and 0.1 (s; 6H) and to be a compound of the formula (I) wherein A is the formula (II) and W is —N(CH$_3$)— and R$^1$ is —O—CH$_2$CH$_2$— (connected to Si at a side of O) and R$^2$ is —O—CH$_2$CH$_2$— (connected to Si at a side of O) and R$^3$ is —CH$_3$ and R$^8$ is —CH$_2$CH$_2$CH$_2$— and x is 2 [i.e. bis(3-(methyl)1,3-dioxa-6-methylaza-2-silacyclooctyl-propyl)disulfide].

Production Example 3 of Organosilicon Compound

In a four-necked flask of 500 mL, 18.0 g of 3-mercaptopropyl dimethoxymethyl silane, 11.9 g of N-methyldiethanol amine and 0.05 g of titanium tetrabutoxide are dissolved in 200 mL of xylene under a nitrogen atmosphere. The temperature is raised to 150° C. and the stirring is continued for 6 hours. Thereafter, the solvent is removed by a rotary evaporator at 20 hPa/40° C., and subsequently the remaining volatile matter is removed by a rotary pump (10 Pa) and a cold trap (dry ice+ethanol) to obtain 21.5 g of 3-mercaptopropyl(methyl)1,3-dioxa-6-methylaza-2-silacyclooctane [organosilicon compound (C-3)] represented by the following chemical formula:

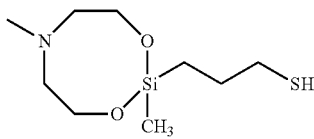

The analytical results of the product by $^1$H-NMR are shown as follows: $^1$H-NMR (CDCl$_3$, 700 MHz, δ:ppm)=3.7 (m; 4H), 2.6 (t; 4H), 2.5 (m; 2H), 2.4 (s; 3H), 1.6 (m; 2H), 0.6 (t; 2H), 0.1 (s; 3H)

Production Example 4 of Organosilicon Compound

In a four-necked flask of 1 L, 18.0 g of 3-mercaptopropyl dimethoxymethyl silane and 11.1 g of triethylamine are dissolved in 300 mL of toluene under a nitrogen atmosphere. To this solution is added 16.2 g of octanoic acid chloride dropwise over 30 minutes, which is stirred for 2 hours. Thereafter, the precipitates are filtered off and the solvent is removed by a rotary evaporator at 20 hPa/40° C. to obtain 29.0 g of 3-octanoylthio-propyl dimethoxymethyl silane.

In a four-necked flask of 500 mL, 29.0 g of 3-octanoylthio-propyl dimethoxymethyl silane, 8.9 g of N-butyldiethanol amine and 0.05 g of titanium tetra-butoxide are subsequently dissolved in 200 mL of xylene under a nitrogen atmosphere. The temperature is raised to 150° C. and the stirring is continued for 2 hours. Thereafter, the solvent is removed by a rotary evaporator at 20 hPa/40° C., and subsequently the remaining volatile matter is removed by a rotary pump (10 Pa) and a cold trap (dry ice+ethanol) to obtain 23.5 g of 3-octanoylthio-propyl(methyl)1,3-dioxa-6-butylaza-2-silacyclooctane [organosilicon compound (C-4)] represented by the following chemical formula:

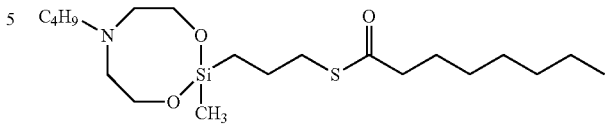

The analytical results of the product by $^1$H-NMR are shown as follows: $^1$H-NMR (CDCl$_3$, 700 MHz, δ:ppm)=3.8 (m; 4H), 2.8 (t; 4H), 2.5 (m; 4H), 2.4 (t; 2H), 1.6 (m; 4H), 1.2 (m; 12H), 1.0 (s; 6H), 0.7 (t; 2H), 0.1 (s; 3H)

Production Example 5 of Organosilicon Compound

In a four-necked flask of 1 L, 18.0 g of 3-mercaptopropyl dimethoxymethyl silane and 11.1 g of triethylamine are dissolved in 300 mL of toluene under a nitrogen atmosphere. To this solution is added 16.2 g of octanoic acid chloride dropwise over 30 minutes, which is stirred for 2 hours. Thereafter, the precipitates are filtered off and the solvent is removed by a rotary evaporator at 20 hPa/40° C. to obtain 29.0 g of 3-octanoylthio-propyl dimethoxymethyl silane.

In a four-necked flask of 500 mL, 29.0 g of 3-octanoylthio-propyl dimethoxymethyl silane, 11.4 g of N-lauryldiethanol amine and 0.05 g of titanium tetra-butoxide are subsequently dissolved in 200 mL of xylene under a nitrogen atmosphere. The temperature is raised to 150° C. and the stirring is continued for 2 hours. Thereafter, the solvent is removed by a rotary evaporator at 20 hPa/40° C., and subsequently the remaining volatile matter is removed by a rotary pump (10 Pa) and a cold trap (dry ice+ethanol) to obtain 30.0 g of 3-octanoylthio-propyl(methyl)1,3-dioxa-6-laurylaza-2-silacyclooctane [organosilicon compound (C-5)] represented by the following chemical formula:

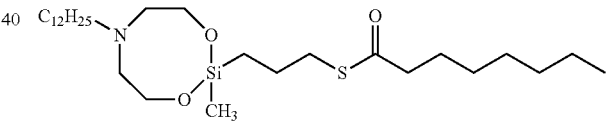

The analytical results of the product by $^1$H-NMR are shown as follows: $^1$H-NMR (CDCl$_3$, 700 MHz, δ:ppm)=3.8 (m; 4H), 2.8 (t; 4H), 2.5 (m; 4H), 2.4 (t; 2H), 1.6 (m; 4H), 1.2 (m; 28H), 1.0 (s; 6H), 0.7 (t; 2H), 0.1 (s; 3H)

<Preparation and Evaluation of Rubber Composition>

A rubber composition is prepared by milling a compounding recipe according to Tables 1-2 in a Banbury mixer. Then, the vulcanization properties of the resulting rubber composition are measured by the following methods. The results are shown in Tables 1-2.

(1) Dynamic Viscoelasticity

Tan δ of the vulcanized rubber is measured using a spectrometer made by Uejima Seisakusho Co., Ltd. under conditions that a frequency is 52 Hz, an initial strain is 10%, a measuring temperature is 60° C. and a dynamic strain is 1%, which is represented by an index on the basis that a value of tan δ of Comparative Example 1 is 100. The smaller the index value, the lower the tan δ and the lower the heat buildup of the rubber composition.

(2) Test for Wear Resistance

The test is carried out at room temperature under a slip ratio of 25% according to JIS K6264-2: 2005 using a Lambourn abrasion tester, and the wear resistance is represented by an index on the basis that a reciprocate of the worn amount in Comparative Example 1 is 100. The larger the index value, the smaller the worn amount, and the better the wear resistance.

TABLE 1

|  |  |  | Comparative Example 1 | Comparative Example 2 | Comparative Example 3 | Comparative Example 4 | Example 1 | Example 2 | Example 3 | Example 4 |
|---|---|---|---|---|---|---|---|---|---|---|
| Compounding recipe | emulsion polymerized SBR-1 *1 | parts by mass | 100.00 | 100.00 | 100.00 | 100.00 | 100.00 | 100.00 | 100.00 | 100.00 |
|  | carbon black-1 N220 *2 |  | 10.00 | 10.00 | 10.00 | 10.00 | 10.00 | 10.00 | 10.00 | 10.00 |
|  | silica *3 |  | 50.00 | 50.00 | 50.00 | 50.00 | 50.00 | 50.00 | 50.00 | 50.00 |
|  | silane compound-1 *4 |  | 5.00 | 6.00 | — | — | — | — | — | — |
|  | silane compound-2 *5 |  | — | — | 5.00 | 6.00 | — | — | — | — |
|  | organosilicon compound (C-1) |  | — | — | — | — | 5.00 | 6.00 | — | — |
|  | organosilicon compound (C-2) |  | — | — | — | — | — | — | 7.00 | 8.40 |
|  | aromatic oil |  | 30.00 | 30.00 | 30.00 | 30.00 | 30.00 | 30.00 | 30.00 | 30.00 |
|  | stearic acid |  | 2.00 | 2.00 | 2.00 | 2.00 | 2.00 | 2.00 | 2.00 | 2.00 |
|  | antioxidant 6PPD *6 |  | 1.00 | 1.00 | 1.00 | 1.00 | 1.00 | 1.00 | 1.00 | 1.00 |
|  | antioxidant TMQ *7 |  | 1.00 | 1.00 | 1.00 | 1.00 | 1.00 | 1.00 | 1.00 | 1.00 |
|  | zinc white |  | 2.50 | 2.50 | 2.50 | 2.50 | 2.50 | 2.50 | 2.50 | 2.50 |
|  | vulcanization accelerator DPG *8 |  | 0.60 | 0.60 | 0.60 | 0.60 | 0.60 | 0.60 | 0.60 | 0.60 |
|  | vulcanization accelerator MBTS *9 |  | 1.00 | 1.00 | 1.00 | 1.00 | 1.00 | 1.00 | 1.00 | 1.00 |
|  | vulcanization accelerator TBBS *10 |  | 0.60 | 0.60 | 0.60 | 0.60 | 0.60 | 0.60 | 0.60 | 0.60 |
|  | sulfur |  | 1.50 | 1.50 | 1.50 | 1.50 | 1.50 | 1.50 | 1.50 | 1.50 |
| Vulcanization properties | tan δ | index | 100 | 98 | 84 | 82 | 86 | 84 | 91 | 90 |
|  | wear resistance | index | 100 | 101 | 91 | 93 | 104 | 106 | 112 | 114 |

TABLE 2

|  |  |  | Example 5 | Example 6 | Example 7 | Example 8 | Example 9 | Example 10 |
|---|---|---|---|---|---|---|---|---|
| Compounding recipe | emulsion polymerized SBR-1 *1 | parts by mass | 100.00 | 100.00 | 100.00 | 100.00 | 100.00 | 100.00 |
|  | carbon black-1 N220 *2 |  | 10.00 | 10.00 | 10.00 | 10.00 | 10.00 | 10.00 |
|  | silica *3 |  | 50.00 | 50.00 | 50.00 | 50.00 | 50.00 | 50.00 |
|  | organosilicon compound (C-3) |  | 5.00 | 6.00 | — | — | — | — |
|  | organosilicon compound (C-4) |  | — | — | 5.00 | 6.00 | — | — |
|  | organosilicon compound (C-5) |  | — | — | — | — | 5.00 | 6.00 |
|  | aromatic oil |  | 30.00 | 30.00 | 30.00 | 30.00 | 30.00 | 30.00 |
|  | stearic acid |  | 2.00 | 2.00 | 2.00 | 2.00 | 2.00 | 2.00 |
|  | antioxidant 6PPD *6 |  | 1.00 | 1.00 | 1.00 | 1.00 | 1.00 | 1.00 |
|  | antioxidant TMQ *7 |  | 1.00 | 1.00 | 1.00 | 1.00 | 1.00 | 1.00 |
|  | zinc white |  | 2.50 | 2.50 | 2.50 | 2.50 | 2.50 | 2.50 |
|  | vulcanization accelerator DPG *8 |  | 0.60 | 0.60 | 0.60 | 0.60 | 0.60 | 0.60 |
|  | vulcanization accelerator MBTS *9 |  | 1.00 | 1.00 | 1.00 | 1.00 | 1.00 | 1.00 |

TABLE 2-continued

|  |  |  | Example 5 | Example 6 | Example 7 | Example 8 | Example 9 | Example 10 |
|---|---|---|---|---|---|---|---|---|
|  | vulcanization accelerator TBBS *10 |  | 0.60 | 0.60 | 0.60 | 0.60 | 0.60 | 0.60 |
|  | sulfur |  | 1.50 | 1.50 | 1.50 | 1.50 | 1.50 | 1.50 |
| Vulcanization properties | tan δ | index | 85 | 84 | 81 | 80 | 77 | 75 |
|  | wear resistance | index | 122 | 123 | 120 | 122 | 116 | 118 |

*1 #1500, emulsion polymerized SBR, made by JSR Corporation
*2 #80, made by Asahi Carbon Co., Ltd.
*3 Nipsil AQ, amde by Nippon Silica Kogyo Co., Ltd. BET surface area = 220 m$^2$/g
*4 bis(3-triethoxysilylpropyl)disulfide
*5 3-octanoylthio-propyl triethoxysilane
*6 Nocrac 6C, made by Ouchi Shinko Chemical Industry Co., Ltd.
*7 Nocrac 224, made by Ouchi Shinko Chemical Industry Co., Ltd.
*8 Sanceler D, made by Sanshin Chemical Industry Co., Ltd.
*9 Sanceler DM, made by Sanshin Chemical Industry Co., Ltd.
*10 Sanceler NS, made by Sanshin Chemical Industry Co., Ltd.

As seen from Tables 1-2, by compounding the organosilicon compound (C) of the invention instead of the conventional silane coupling agent (*4, *5) can be largely reduced tan δ of the rubber composition or the hysteresis loss and highly improved the wear resistance while holding the low heat buildup.

The invention claimed is:

1. An organosilicon compound, characterized by having a cyclic structure with nitrogen atom and silicon atom, and one or more sulfur atoms in its molecule, and having a bonding site of at least one selected from the group consisting of a hydrogen atom, methyl group and hydroxyl group to silicon atom, which is represented by the following general formula (I):

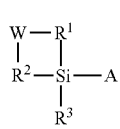

(I)

wherein A is a group containing at least one selected from the group consisting of polysulfide group, thioester group, thiol group, dithiocarbonate group, dithioacetal group, hemithioacetal group, vinylthio group, α-thiocarbonyl group, β-thiocarbonyl group, S—CO—CH$_2$—O moiety, S—CO—CO moiety and S—CH$_2$—Si moiety;

W is represented by —NR$^4$—, —O— or —CR$^4$R$^5$—, wherein R$^5$ is —R$^6$ or —C$_m$H$_{2m}$—R', provided that R$^7$ is —NR$^4$R$^6$, —NR$^4$—NR$^4$R$^6$ or —N═NR$^4$, and R$^4$ is —C$_n$H$_{2n+1}$ and R$^6$ is —C$_q$H$_{2q+1}$, and m, n and q are independently 0-20;

R$^1$ and R$^2$ are independently -M-C$_l$H$_{2l}$—, wherein M is —O— or —CH$_2$— and l is 0-10, provided that M in one or more of R$^1$ and R$^2$ is —O—; and R$^3$ is a hydrogen atom, methyl group or hydroxyl group.

2. An organosilicon compound according to claim 1, wherein A in the general formula (I) contains at least one of polysulfide group and thioester group.

3. An organosilicon compound according to claim 1, wherein A in the general formula (I) is represented by the following general formula (II), (III) or (IV):

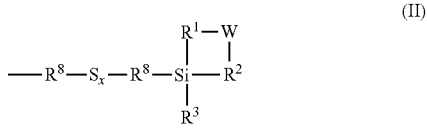

(II)

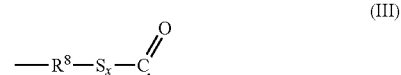

(III)

(IV)

wherein W, R$^1$, R$^2$ and R$^3$ in the formula (II) have the same meanings as mentioned above;

R$^8$ in the formulae (II), (III) and (IV) is represented by the following general formula (V) or (VI):

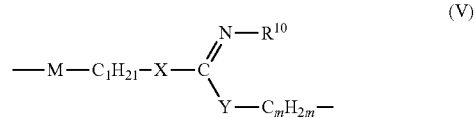

(V)

(VI)

or by -M-C$_l$H$_{2l}$—, wherein M, l and m have the same meanings as mentioned above, X and Y are independently —O—, —NR$^4$— or —CH$_2$— and R$^{10}$ is -OR$^4$, —NR$^4$R$^6$ or —R$^4$, and R$^{11}$ is —NR$^4$—, —NR$^4$—NR$^4$— or —N═N—, provided that R$^4$ and R$^6$ have the same meanings as mentioned above;

R$^9$ in the formula (III) is represented by the following general formula (VII) or (VIII):

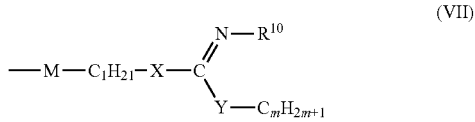

(VII)

(VIII)

or by —C$_l$—H$_{2l}$—R$^{12}$, wherein M, X, Y, $R^{10}$, $R^7$, l and m have the same meanings as mentioned above, $R^{12}$ is $-NR^4R^6$, $-NR^4-NR^4R^6$, $-N=NR^4$ or $-M-C_mH_{2m+1}$ or an aromatic hydrocarbon group having a carbon number of 6-20, provided that $R^4$, $R^6$, M, l and m have the same meanings as mentioned above;

x in the formulae (II) and (III) is 1-10.

4. An organosilicon compound according to claim 1, wherein M is —O—.

5. An organosilicon compound according to claim 3, wherein W is represented by $-NR^4-$, wherein $R^4$ has the same meaning as mentioned above, $R^1$ and $R^2$ are independently represented by $-O-C_lH_{2l}-$, wherein l has the same meaning as mentioned above, $R^3$ is a hydrogen atom, methyl group or hydroxyl group, $R^8$ is represented by $-C_lH_{2l}-$, wherein l has the same meaning as mentioned above, and $R^9$ is a linear or branched alkyl group represented by $-C_lH_{2l+1}$, wherein l has the same meaning as mentioned above, or an aromatic hydrocarbon group having a carbon number of 6-20.

6. An organosilicon compound according to claim 3, wherein W is represented by —O— or $-CR^4R^6-$, wherein $R^4$ and $R^6$ have the same meanings as mentioned above, $R^1$ and $R^2$ are independently represented by $-O-C_lH_{2l}-$, wherein l has the same meaning as mentioned above, $R^3$ is a hydrogen atom, methyl group or hydroxyl group, $R^8$ is represented by $-C_lH_{2l}-$, wherein l has the same meaning a mentioned above, and $R^9$ is represented by $-C_lH_{2l+1}$, wherein l has the same meaning as mentioned above.

7. A rubber composition, characterized by compounding an inorganic filler (B) and an organosilicon compound (C) as claimed in claim 1 into a rubber component (A) consisting of natural rubber and/or diene-based synthetic rubber.

8. A rubber composition according to claim 7, wherein 5-140 parts by mass of the inorganic filler (B) is compounded based on 100 parts by mass of the rubber component (A) consisting of natural rubber and/or diene-based synthetic rubber; and the organosilicon compound (C) is included in an amount of 1-20 mass % of the compounding amount of the inorganic filler (B).

9. A rubber composition according to claim 7, wherein the inorganic filler (B) is silica or aluminum hydroxide.

10. A rubber composition according to claim 9, wherein the silica has a BET surface area of 40-350 m$^2$/g.

11. A tire, characterized by using a rubber composition as claimed in claim 7.

12. A primer composition, characterized by including an organosilicon compound as claimed in claim 1.

13. A paint composition, characterized by including an organosilicon compound as claimed in claim 1.

14. An adhesive, characterized by including an organosilicon compound as claimed in claim 1.

* * * * *